(12) United States Patent
Zhen et al.

(10) Patent No.: US 11,497,722 B2
(45) Date of Patent: Nov. 15, 2022

(54) USE OF METFORMIN SALT IN THE TREATMENT OF CEREBRAL INFARCTION

(71) Applicant: SOOCHOW UNIVERSITY, Suzhou (CN)

(72) Inventors: Xuechu Zhen, Suzhou (CN); Zongyin Liu, Suzhou (CN); Linyi Qian, Suzhou (CN); Huimin Cao, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 153 days.

(21) Appl. No.: 16/772,667

(22) PCT Filed: Dec. 12, 2018

(86) PCT No.: PCT/CN2018/120479
§ 371 (c)(1),
(2) Date: Jun. 12, 2020

(87) PCT Pub. No.: WO2019/120111
PCT Pub. Date: Jun. 27, 2019

(65) Prior Publication Data
US 2021/0069130 A1    Mar. 11, 2021

(30) Foreign Application Priority Data

Dec. 18, 2017  (CN) .......................... 201711364772.3
Jan. 16, 2018  (CN) .......................... 201810039233.0
Jun. 15, 2018  (CN) .......................... 201810623095.0

(51) Int. Cl.
| | |
|---|---|
| *A61K 31/155* | (2006.01) |
| *A61K 31/191* | (2006.01) |
| *C07C 279/26* | (2006.01) |
| *C07C 59/10* | (2006.01) |
| *C07C 51/41* | (2006.01) |
| *A61P 9/10* | (2006.01) |

(52) U.S. Cl.
CPC .............. *A61K 31/155* (2013.01); *A61P 9/10* (2018.01)

(58) Field of Classification Search
CPC ....... C07C 279/26; C07C 59/10; C07C 51/41; A61K 31/155; A61K 31/191; A61P 9/10
See application file for complete search history.

(56) References Cited

U.S. PATENT DOCUMENTS

| | | | |
|---|---|---|---|
| 2012/0178813 A1* | 7/2012 | Mylari ...................... | A61P 3/10 514/560 |
| 2014/0256820 A1* | 9/2014 | Takata ..................... | A61P 25/08 514/635 |
| 2017/0128397 A1* | 5/2017 | Liu ......................... | A61K 31/14 |

FOREIGN PATENT DOCUMENTS

| | | | | |
|---|---|---|---|---|
| CN | 102093261 | * | 6/2011 | ........... C07C 279/26 |
| CN | 102093261 A | | 6/2011 | |

OTHER PUBLICATIONS

Yu, Yongfei et al., "Clinical Study of Thrombolytic Therapy with Intravenous Recombinant Tissue-Type Plasminogen Activator for Patients with Acute Cerebral Infarction", Journal of Critical Care in Internal Medicine, vol. 20, No. 4, Aug. 15, 2014, pp. 244-245, 280.

* cited by examiner

*Primary Examiner* — Irina Neagu
(74) *Attorney, Agent, or Firm* — SZDC Law P.C.

(57) ABSTRACT

The present invention provides the use of a metformin salt, particularly metformin monothreonate, in the preparation of a medicament for treating cerebral infarction. The metaformin monothreonate of the present invention has an excellent effect in the treatment of cerebral infarction. The present invention also provides a method for preparing metformin monothreonate and a composition comprising metformin monothreonate.

7 Claims, 4 Drawing Sheets

USE OF METFORMIN SALT IN THE TREATMENT OF CEREBRAL INFARCTION

This application is the National Stage Application of PCT/CN2018/120479, filed on Dec. 12, 2018, which claims priority to Chinese Patent Application Nos. 201711364772.3, filed on Dec. 18, 2017, 201810039233.0, filed on Jan. 16, 2018, and 201810623095.0, filed on Jun. 15, 2018, all of which are incorporated by reference for all purposes as if fully set forth herein.

FIELD OF THE INVENTION

The present invention relates to the field of pharmaceutical preparations. In particular, the present invention relates to the use of metformin monothreonate and various other salts in the preparation of medicaments for treating cerebral infarction. The present invention also relates to a method for preparing metformin monothreonate and various other salts.

DESCRIPTION OF THE RELATED ART

Cerebral infarction can cause acute damage to brain tissue and is the second leading cause of death worldwide. Neurons will become apoptosis without oxygen and nutrient supplement, leading to permanent damage to the brain without efficient treatment.

At present, the only drug approved by FDA for the treatment of brain ischemic stroke is recombinant human tissue-type plasminogen activators(tPA). The administration of tPA in a short time after the occurrence of cerebral infarction contributes to the degradation of the thrombus, thus decrease acute mortality and chronic morbidity. However, less than 5% of patients benefit this treatment due to the narrow therapeutic window.

Therefore, there is still a need for enormous efforts to develop more potent and efficient therapy to brain ischemic stroke.

SUMMARY OF THE INVENTION

In one aspect, the present invention relates to the use of a metformin salt in the preparation of a medicament for preventing and/or treating cerebral infarction in a subject.

In another aspect, the present invention relates to the use of a metformin salt in the preparation of a medicament for treating cerebral infarction in a subject, including combination with other drugs used for treating cerebral infarction.

In one embodiment, the metformin salt is one or more selected from the group consisting of metformin monothreonate, metformin tartrate, metformin citrate, metformin mesylate, metformin maleate, and metformin hydrobromide. In one embodiment, the metformin salt is preferably metformin monothreonate.

In one embodiment, the subject is a non-diabetic patient.

In one embodiment, the medicament is administered orally or by injection.

In one embodiment, the metformin salt, preferably metformin monothreonate is used to treat cerebral infarction n a subject.

In one embodiment, the drug for treating cerebral infarction is a human tissue-type plasminogen activator. In one embodiment, the human tissue-type plasminogen activator is a recombinant human tissue-type plasminogen activator.

In another aspect, the present invention relates to metformin monothreonate. In one embodiment, the chemical formula (I) of metformin monothreonate is as follow:

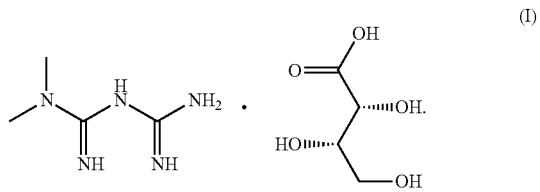

In another aspect, the present invention relates to a method for the preparation of metformin monothreonate, which includes reacting metformin and threonate under heating.

In one embodiment, the threonate salt used in the preparation of metformin monothreonate is an alkali metal salt or an alkaline earth metal salt of threonic acid, and preferably magnesium threonate.

In one embodiment, the heating temperature of the reaction is 65-75° C., and preferably 70° C.

In one embodiment, the preparation of metformin monothreonate further includes dissolving the reactants in an organic solvent, then filtering and drying. The organic solvent used in this invention is an alcohol, an ether, a nitrile, a ketone or an ester solvent with 1 to 5 carbon atoms, preferably ethanol.

In another aspect, the present invention relates to a pharmaceutical composition including metformin monothreonate as described above, or metformin monothreonate combined with one or more pharmaceutically acceptable carriers.

In one embodiment, the pharmaceutical composition can be administered orally or by injection. In one embodiment, the pharmaceutical composition is a tablet or injection.

The metaformin monothreonate of the present invention exhibits remarkable safety and efficacy, and high bioavailability in the prevention and treatment of cerebral ischemia.

DETAILED DESCRIPTION OF THE PREFERRED EMBODIMENTS

Figure 1:
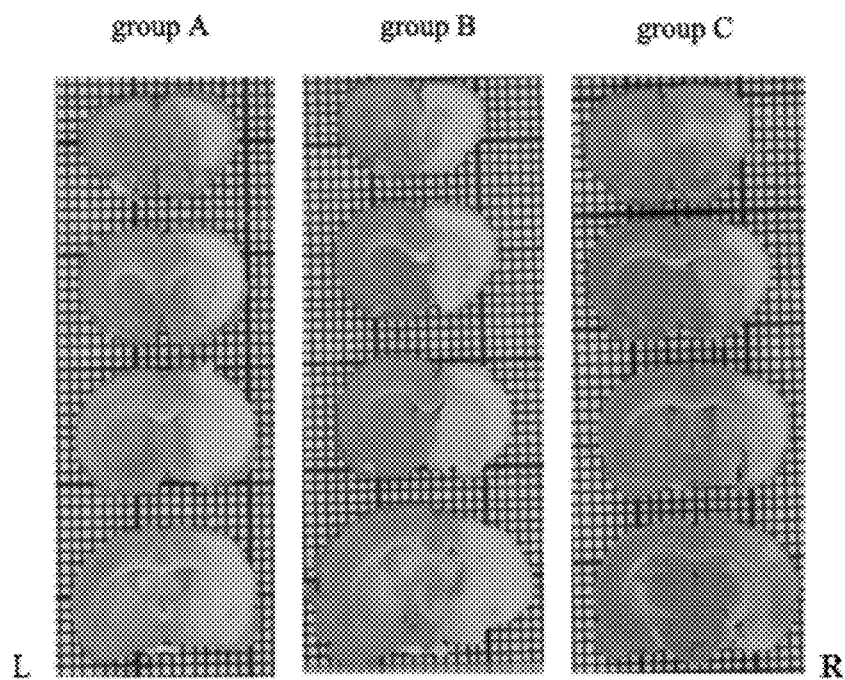
FIG. 1 shows rat brain slices staining with TTC (L and R represent the left and right brain hemispheres respectively).

Unless otherwise defined below, the meaning of all technical and scientific terms used herein is intended to be the same as those commonly understood by those skilled in the art. References to the technologies used herein are intended to refer to technologies commonly understood in the art, including changes in the technologies or replacements by equivalent technologies that are obvious to those skilled in the art. Although it is believed that the following terms are well understood by those skilled in the art, the following definitions are still set forth to better explain the present invention.

The terms "including," "comprising," "having," "containing" or "involving" and other variations thereof as used herein are inclusive or open-ended, and do not exclude other unlisted elements or method steps.

A. Pharmaceutical Use of Metformin Salt

The present inventors unexpectedly find that metformin salts, especially metformin monothreonate, can prevent and/or treat cerebral infarction. Accordingly, the present invention relates to the use of a metformin salt in the preparation of a medicament for preventing and/or treating cerebral infarction. The present invention also relates to metformin salts, which are used in the prevention and/or treatment of cerebral infarction. The present invention also relates to a method for preventing and/or treating cerebral infarction, which comprises administering a prophylactically and/or therapeutically effective amount of a metformin salt to a subject.

As used herein, the term "cerebral infarction" refers to a group of diseases that cause brain tissue damage due to blood circulation disorders caused by obstruction of blood vessels in the brain. "Cerebral infarction" is also known as "ischemic stroke." Unless otherwise stated, "cerebral infarction," "cerebral arterial thrombosis," and "ischemic stroke" are used interchangeably herein.

As used herein, the term "treatment" means that an individual suffering from a disease or disease state after administration of the medicament of the present invention shows partial or complete remission of the symptoms or does not show continuous aggravation after treatment. Therefore, the treatment includes curing. As used herein, "therapeutic effect" means the effect caused by treatment, which changes, and usually reduces or ameliorates the symptoms of the disease or disease state, or cures the disease or disease state.

The term "prevention" refers to preventing the occurrence and development of a potential disease by administering a drug or treatment before the related disease or disease state occurs or before appreciable symptoms and/or signs appear. Unless otherwise stated, the term "treatment" in the present invention does not include prophylactic administration.

As used herein, "prophylactically or therapeutically effective amount" refers to an amount of a substance, a compound, or a composition comprising a compound that is at least sufficient to produce a prophylactic or therapeutic effect after administration to a subject. Therefore, it is the amount necessary to prevent, prevent, cure, ameliorate, arrest or partially arrest the symptoms of a disease or condition.

In one embodiment, the metformin salt is used to treat cerebral infarction in a subject.

In one embodiment, the metformin salt is selected from the group consisting of metformin monothreonate, metformin tartrate, metformin citrate, metformin mesylate, metformin maleate, and metformin hydrobromide. In one embodiment, the metformin salt is preferably metformin monothreonate.

Accordingly, in one embodiment, the present invention provides the use of metformin monothreonate in the preparation of a medicament for preventing and/or treating cerebral infarction. In one embodiment, the present invention further provides metformin monothreonate, which is used to prevent and/or treat cerebral infarction. In one embodiment, the present invention also relates to a method for preventing and/or treating cerebral infarction, which comprises administering a prophylactically and/or therapeutically effective amount of metformin monothreonate to a subject. In one embodiment, the metformin monothreonate is used to treat cerebral infarction in a subject.

"Subject" as used herein includes human or non-human animals, especially human individuals, including human individuals (called patients) suffering from a disease (especially cerebral infarction as described herein).

The efficacy of metformin for cerebral infarction is independent of the glucose-decreasing effect of metformin. Therefore, "subject" as used herein also includes non-diabetic patients. In one embodiment, the present invention provides the use of a metformin salt, preferably metformin monothreonate, in the preparation of a medicament for treating cerebral infarction in a non-diabetic subject. In one embodiment, the present invention provides a metformin salt, preferably metformin monothreonate, which is used to treat cerebral infarction in a non-diabetic subject. In one embodiment, the present invention provides a method for treating cerebral infarction in a non-diabetic subject, which comprises administering to the subject a therapeutically effective amount of a metformin salt, preferably metformin monothreonate.

The present invention also relates to the combined use of a metformin salt with other drugs for treating cerebral infarction. In one embodiment, the present invention provides the use of a metformin salt, preferably metformin monothreonate, in the preparation of a medicament for treating cerebral infarction in a subject, where the medicament is used in combination with a drug for treating cerebral infarction.

The term "drug for treating cerebral infarction" as used herein includes drugs known in the art that can be used for treating cerebral infarction, including but not limited to, human tissue-type plasminogen activators, and urokinase-type plasminogen activators. In one embodiment, the drug for treating cerebral infarction is a human tissue-type plasminogen activator, preferably a recombinant human tissue-type plasminogen activator. In one embodiment, the metformin salt is metformin monothreonate.

The present invention also relates to a composition comprising a combination of a metaformin salt of the present invention, preferably metaformin monothreonate and at least one drug for treating cerebral infarction. In one embodiment, the drug for treating cerebral infarction is a human tissue-type plasminogen activator, preferably a recombinant human tissue-type plasminogen activator. In one embodiment, the metformin salt is metformin monothreonate.

Therefore, in one embodiment, the present invention provides the use of a composition comprising a metformin salt, preferably metformin monothreonate, and at least one drug for treating cerebral infarction, in the preparation of a drug for preventing and/or treating cerebral infarction. In one embodiment, the present invention also provides a composition comprising a metformin salt, preferably metformin monothreonate, and at least one drug for treating cerebral infarction, which is used to prevent and/or treat cerebral infarction. In one embodiment, the present invention also relates to a method for preventing and/or treating cerebral infarction, which comprises administering a prophylactically and/or therapeutically effective amount of a composition comprising a metformin salt, preferably metformin monothreonate, and at least one drug for treating cerebral infarction, to a subject.

The metformin salt of the present invention, especially metformin monothreonate, has good neuroprotective effect and distribution in brain tissues, and can be distributed more quickly in the brain tissues with a higher amount, so it is suitable for use in the preparation of drugs for preventing and/or treating cerebral infarction.

B. Metformin Monothreonate, Pharmaceutical Composition, and Preparation Method

The present invention also relates to metformin monothreonate. In one embodiment, the chemical formula (I) of metformin monothreonate is as below:

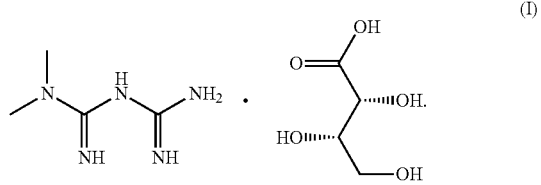

(I)

The metformin monothreonate of the present invention is suitable for use in the preparation of a pharmaceutical preparation. Therefore, the present invention also relates to a pharmaceutical composition including metformin monothreonate of the present invention, and one or more pharmaceutically acceptable carriers.

The term "pharmaceutically acceptable carrier" as used herein refers to a diluent, adjuvant, excipient, or vehicle administered with a therapeutic agent, which is suitable for contact with tissues of human and/or other animals within the scope of reasonable medical judgment, without undue toxicity, irritation, allergic reactions, or other problems or complications corresponding to reasonable benefit/risk ratio. Examples of suitable pharmaceutically acceptable carriers are described in Remington's Pharmaceutical Sciences (1990). In one embodiment, the pharmaceutically acceptable carrier includes but is not limited to: solvents, stabilizers, surfactants, lubricants, fillers, sweeteners, and disintegrants.

The metaformin monothreonate of the present invention or the pharmaceutical composition of the present invention can act systemically and/or locally. For this purpose, they can be administered through suitable routes, for example by injection, intravenous, intraarterial, subcutaneous, intraperitoneal, intramuscular or transdermal administration; or by oral, buccal, nasal, transmucosal, or topical administration or by inhalation.

For these administration routes, the pharmaceutical composition of the present invention can be administered in a suitable dosage form. The dosage form includes but is not limited to tablets, capsules, lozenges, powders, sprays, ointments, and injections, etc. In one embodiment, the pharmaceutical composition is an injection, a tablet, or a solution, and preferably an injection.

In one embodiment, the metformin monothreonate is prepared into a tablet comprising or consisting of metformin monothreonate, lactose, dextrin, corn starch, Povidone K30, magnesium stearate, and silica. In one embodiment, the metformin monothreonate is prepared into an injection, which comprises or consists of metformin monothreonate, disodium hydrogen phosphate, and HCl or NaOH (appropriate amount).

In one embodiment, the present invention also provides the use of a pharmaceutical composition comprising a metformin salt, preferably metformin monothreonate, in the preparation of a drug for preventing and/or treating cerebral infarction. In one embodiment, the present invention also provides a pharmaceutical composition comprising a metformin salt, preferably metformin monothreonate, which is used to prevent and/or treat cerebral infarction. In one embodiment, the present invention also relates to a method for preventing and/or treating cerebral infarction, which comprises administering a prophylactically and/or therapeutically effective amount of a pharmaceutical composition comprising a metformin salt, preferably metformin monothreonate, to a subject.

The present invention further relates to a method for preparing metformin monothreonate, which comprises reacting metformin and threonic acid with heating. In one embodiment, the "threonate salt" used in the preparation of metformin monothreonate includes magnesium threonate.

In one embodiment, the heating occurs at 65-75° C., and preferably 70° C.

In one embodiment, the method further comprises dissolving the reactants in an organic solvent, and then filtering and drying, where the organic solvent includes an alcohol solvent having 1 to 5 carbon atoms.

The term "alcohol solvent" as used herein preferably means an alcohol having 1 to 5 carbon atoms, which includes but is not limited to methanol, ethanol, 1-propanol, 2-propanol, 1-butanol, 2-Butanol and tert-butanol. In one embodiment, the alcohol solvent is ethanol.

"Drying" in the present invention is preferably carried out under reduced pressure at any temperature (preferably room temperature) until the content of the remaining solvent is reduced to a range generally required in the pharmaceutical field. In one embodiment, the drying used in the preparation of metformin monothreonate in the present invention is vacuum drying.

EXAMPLES

The present invention will be explained in further detail in conjunction with examples below. The examples of the present invention are only intended to illustrate the technical solution, and not to limit the scope of the present invention.

Example 1

Preparation of Metformin

Structural Formula

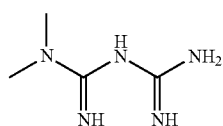

Synthesis Route

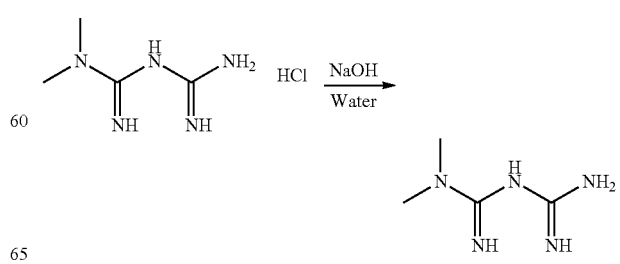

Synthesis Process

In a 500 ml single-neck flask, metformin hydrochloride (55 g, 0.33 mol) was dissolved in water (200 ml), and then sodium hydroxide (14 g, 0.35 mol) was added at room temperature and dissolved under stirring, then the solution was crystallized at 0-5° C. (where burst of crystallization might occur, in this case, the crude crystal was dissolved by heating, and then recrystallized). After 1 h, the solution was filtered, and the filter cake was subjected to rotary evaporation in aqueous ethanol to obtain a white solid (7.8 g). Yield 18%.

Example 2

Preparation of Metformin Monothreonate (SHY01-001)

Structural Formula

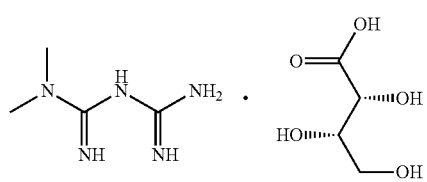

Synthesis Route

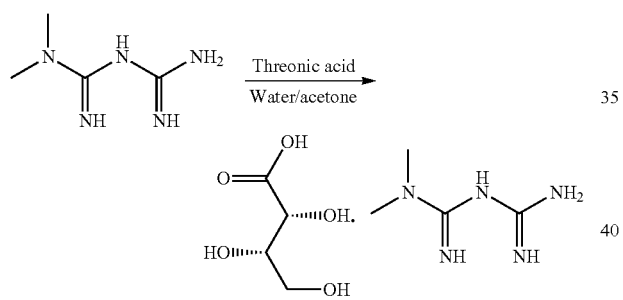

Synthesis Process

To a 1 L single-neck flask, a threonic acid paste (61 g) was added, and then water (100 ml) was added to dissolve it. Metformin (51.6 g) and water (100 g) were added, and continuously stirred until the content was dissolved. The reaction solution was added dropwise to acetone (1 L), and a solid was precipitated out, which was filtered and dried to obtain a white solid (18 g, yield 17%).

$^1$H NMR (400 MHz, D$_2$O) δ 2.94(s, 6H), 3.58 (m, 4H), 3.91 (m, 2H), 3.99 (m, 2H)

Example 3

Preparation of Metformin Tartrate (SHY01-002)

Structural Formula

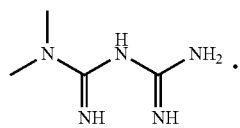

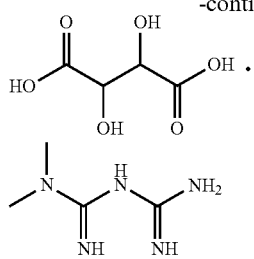

Synthesis Route

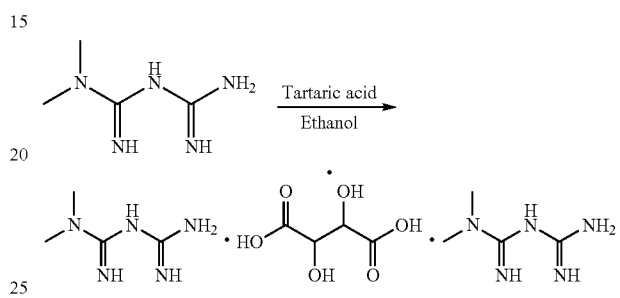

Synthesis Process

To a 100 ml single-neck flask, a mixture of metformin (430 mg, 3.3 mmol) and tartaric acid (1 g, 6.7 mmol) was heated to 70° C. in absolute ethanol (10 ml) to dissolve the content, then continuously stirred for 1 h, and filtered while hot. The filtrate was crystallized at −10° C., and filtered after 2 h. The obtained product was dried and weighed to obtain a white solid (350 mg). Yield 44%.

$^1$H NMR (400 MHz, D$_2$O) δ 2.96(s, 12H), 4.24(s, 2H)

Example 4

Preparation of Metformin Citrate (SHY01-003)

Structural Formula

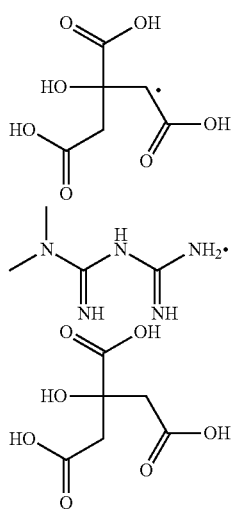

Synthesis Route

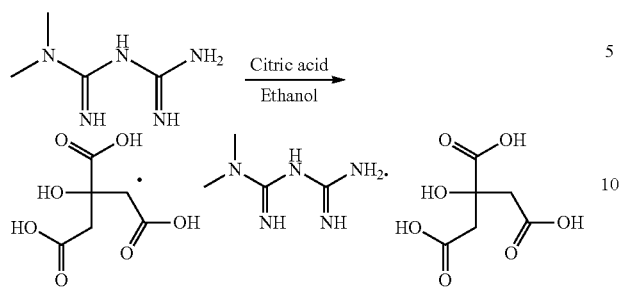

Synthesis Process

To a 100 ml single-neck flask, a mixture of metformin (430 mg, 3.3 mmol) and citric acid monohydrate (1.4 g, 6.7 mmol) was heated to 70° C. in absolute ethanol (10 ml) to dissolve the content, then continuously stirred for 1 h, and filtered while hot. The filtrate was crystallized at −10° C., and filtered after 2 h. The filter cake was prone to moisture adsorption. After collection, it was transferred to a single-neck flask. The residual water was removed with absolute ethanol, and then the remainder was dried under suction by a vacuum oil pump. After purging with nitrogen, a white solid (310 mg) was obtained. Yield 18.3%.

$^1$H NMR (400 MHz, D$_2$O) δ 2.67-2.85 (m, 4H), 2.98(s, 6H)

Example 5

Preparation of Metformin Methanesulfonate (SHY01-004)

Structural Formula

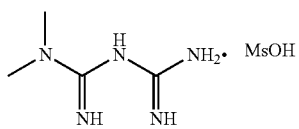

Synthesis Route

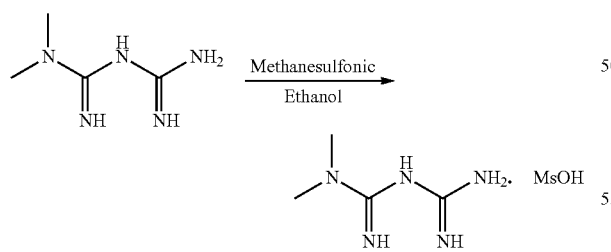

Synthesis Process

To a 100 ml single-neck flask, a mixture of metformin (430 mg, 3.3 mmol) and methanesulfonic acid (640 mg, 6.7 mmol) was heated to 70° C. in absolute ethanol (10 ml) to dissolve the content, then continuously stirred for 1 h, and filtered while hot. The filtrate was crystallized at −10° C., and filtered after 2 h. The obtained product was dried and weighed to obtain a white solid (450 mg). Yield 60.6%.

$^1$H NMR (400 MHz, D$_2$O) δ 3.08(s, 6H), 2.71 (s, 3H)

Example 6

Preparation of Metformin Maleate (SHY01-005)

Structural Formula

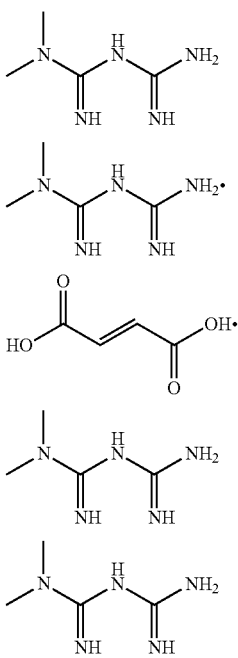

Synthesis Route

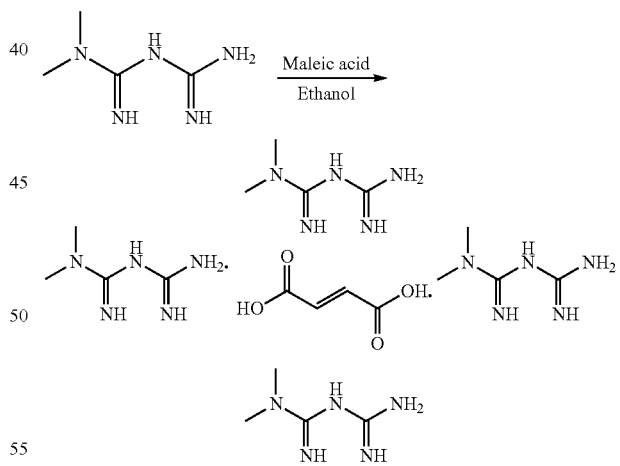

Synthesis Process

To a 100 ml single-neck flask, a mixture of metformin (430 mg, 3.3 mmol) and maleic acid (777 mg, 6.7 mmol) was heated to 70° C. in absolute ethanol (10 ml) to dissolve the content, then continuously stirred for 1 h, and filtered while hot. The filtrate was crystallized at −10° C., and filtered after 2 h. The obtained product was dried and weighed to obtain a white solid (380 mg). Yield 72.8%.

$^1$H NMR (400 MHz, D$_2$O) δ 2.98(s, 24H), 6.23 (s, 2H)

Example 7

Preparation of Metformin Hydrobromide (SHY01-006)

Structural Formula

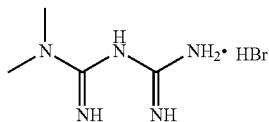

Synthesis Route

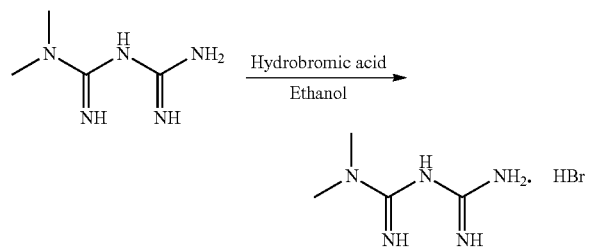

Synthesis Process

To a 100 ml single-neck flask, a mixture of metformin (430 mg, 3.3 mmol) and hydrobromic acid (40%) (1.33 mg, 6.7 mmol) was heated to 70° C. in absolute ethanol (10 ml) to dissolve the content, then continuously stirred for 1 h, and filtered while hot. The filtrate was crystallized at −10° C., and filtered after 2 h. The obtained product was dried and weighed to obtain a white solid (480 mg). Yield 69.3%.

$^1$H NMR (400 MHz, D$_2$O) δ 3.10(s, 6H)

Example 8

Test of Drug Distribution of SHY01-001 and SHY01-005 in Brain Tissue

90 SD rats (7-8 weeks old, 250±20 grams) were kept in an animal room for one week (where the temperature was maintained at 18-26° C., the light and dark period were 12 hrs each, and the test animals were allowed to free access to feed and water) After 1 week, 81 rats with good physical conditions were selected and included in this test. The day before the test, the three groups of rats were fasted for 12 hours, but allowed to free access to water. On the day of the test, the animals were weighed, and the actual dosing volume for each rat was calculated according to the following formula.

$$\text{Dosing volume(mL)} = \left(\frac{\text{Dosage (mg·kg}^{-1})}{\text{Concentration of test solution (mg·mL}^{-1})}\right) \times \text{Body weight(kg)}$$

The body weight of the three groups of SD rats and the actual dosage of 50 mg·kg$^{-1}$ sample orally taken once were recorded in detail. The rats are allowed to resume eating 3 hrs after administration and they had free access to water during the test.

After administration, the three groups of rats were sacrificed respectively at 30 min, 1 h, 2 h, 4 h, 6 h, 8 h, 12 h, 16 h and 24 h. The brain was removed and washed with ice-cold saline. After the water was absorbed, all or part of the tissue was taken and accurately weighed according to a specific homogenization ratio, added to the saline, and homogenized at a high speed (15,000 rpm) in an ice bath. The tissue homogenate was stored in a refrigerator at a low temperature of −80° C. for sample analysis.

The concentrations of metformin hydrochloride, SHY01-001 and SHY01-005 in rat brain tissue were determined by LC-MS/MS analysis. The test results are shown in Tables 1-3 below.

TABLE 1

Test results for the concentration of SHY01-001 in rat brain tissue

| | SHY01-001 Concentration (ng/mL) | | | | | |
|---|---|---|---|---|---|---|
| Time (hr) | Test #1 | Test #2 | Test #3 | Mean | SD | CV |
| 0.5 | 170 | 210 | 64.3 | 148.1 | 75.3 | 51% |
| 1 | 327 | 649 | 600 | 525.3 | 173.5 | 33% |
| 2 | 706 | 762 | 823 | 763.7 | 58.5 | 8% |
| 4 | 505 | 413 | 565 | 494.3 | 76.6 | 15% |
| 6 | 384 | 387 | 675 | 482.0 | 167.1 | 35% |
| 8 | 293 | 259 | 237 | 263.0 | 28.2 | 11% |
| 12 | 150 | 100.2 | 90.3 | 113.5 | 32.0 | 28% |
| 16 | 123 | 78.5 | 65.4 | 89.0 | 30.2 | 34% |
| 24 | 50.3 | 12.6 | 24.9 | 29.3 | 19.2 | 66% |

TABLE 2

Test results for the concentration of metformin hydrochloride in rat brain tissue

| | Metformin hydrochloride Concentration (ng/mL) | | | | | |
|---|---|---|---|---|---|---|
| Time (hr) | Test #1 | Test #2 | Test #3 | Mean | SD | CV |
| 0.5 | 56.3 | 15.3 | 23.6 | 31.7 | 21.7 | 68% |
| 1 | 178.4 | 82.5 | 50.9 | 103.9 | 66.4 | 64% |
| 2 | 205.6 | 105.9 | 212.5 | 174.7 | 59.7 | 34% |
| 4 | 246.5 | 208.7 | 280.9 | 245.4 | 36.1 | 15% |
| 6 | 300.2 | 260.4 | 305.8 | 288.8 | 24.8 | 9% |
| 8 | 202.6 | 150.6 | 198.7 | 176.6 | 36.8 | 21% |
| 12 | 132.5 | 100.8 | 120.5 | 117.9 | 16.0 | 14% |
| 16 | 92.2 | 50.7 | 84.2 | 75.7 | 22.0 | 29% |
| 24 | 25.4 | 10.2 | 50.2 | 28.6 | 20.2 | 71% |

TABLE 3

Test results for the concentration of SHY01-005 in rat brain tissue

| | SHY01-005 Concentration (ng/mL) | | | | | |
|---|---|---|---|---|---|---|
| Time (hr) | Test #1 | Test #2 | Test #3 | Mean | SD | CV |
| 0.5 | 56.5 | 12.6 | NA | 34.6 | 31.0 | 90% |
| 1 | 92.5 | 62.5 | 40.9 | 65.3 | 25.9 | 40% |
| 2 | 153.4 | 145.8 | 87 | 128.7 | 36.3 | 28% |
| 4 | 206 | 198.2 | 105.6 | 169.9 | 55.9 | 33% |
| 6 | 280.6 | 265.4 | 150.8 | 232.3 | 71.0 | 31% |
| 8 | 350.6 | 200.5 | 230.5 | 260.5 | 79.4 | 30% |
| 12 | 250.6 | 155.4 | 158.2 | 188.1 | 54.2 | 29% |
| 16 | 152.6 | 56.7 | 64.2 | 91.2 | 53.3 | 59% |
| 24 | 15.4 | 14.2 | 60.3 | 30.0 | 26.3 | 88% |

As shown in Table 1-3, the concentration of SHY01-001 in brain tissue is greater than that of metformin hydrochloride and SHY01-005 from the time of 0.5 hr, and reaches a peak of 763.7 ng/mL at 2 hrs, and then decreases. In contrast, metformin hydrochloride and SHY01-005 reach the peak concentrations after 6-8 hrs, and their peak concentrations are much lower than that of SHY01-001 (SHY01-001 vs. metformin hydrochloride=763.7 vs. 288.8 ng/mL; and SHY01-001 vs. SHY01-005=763.7 vs. 260.5 ng/mL). This shows that SHY01-001 can be quickly and massively distributed into brain tissue and has excellent bioavailability.

Example 9

The Effect of SHY01-001 in Preventing Brain Ischemia-Reperfusion Injury

A total of 13 male clean SD rats (weight 200-300 g) were used to construct the MCAO (middle cerebral artery occlusion) model (for the model construction method, see Enrique Zea Longa et al., Stroke, Vol 20, No. 1, 1989; and A. Tamura et al., Journal of Cerebral Blood Flow and Metabolism, 1:53-60, 1981), in which the ischemic time was 90 min, then blood flow was restored, and subsequent experiments were performed 24 hrs after reperfusion.

24 hrs after MCAO, each of the rats was immediately given the positive control metformin hydrochloride or SHY01-001 at a dosage of 50 mg/kg/day by intraperitoneal injection once a day for 3 consecutive days. The solvent was saline. The rats in the control group were injected with an equal amount of saline. The 13 MCAO rats were divided into three groups, including group A) saline+MCAO group (4 rats); group B) metformin hydrochloride+MCAO group (3 rats); and group C) SHY01-001+MCAO group (6 rats).

Three days after the administration, the whole brain of the rat was taken and sliced. The whole brain of the rat was cut into 4 slices with a thickness of 2 mm using a single-sided blade. The first cut was at the midpoint of the line between the anterior pole of the brain and the optic chiasm; the second cut was at the position of the optic chiasm; the third cut was at the position of the infundibular stalk; the fourth cut is between the infundibular stalk and the posterior caudal lobe; and the fifth cut was approximately at the posterior caudal lobe.

Subsequently, the brain slices were placed in a freshly prepared 2% 2,3,5-triphenyltetrazolium chloride (TTC) solution and stained in the dark at 37° C. in a water bath for about 10 min. After staining, the brain slices were immobilized in 4% paraformaldehyde for 24 h. The brain slices of the three groups of rats are shown in FIG. 1. Then the cerebral infarction area was measured.

Method for measuring cerebral infarction area: images were scanned, and the infarction-side striatum, cortex and hemispheric infarct volume and the contralateral striatum, cortex and hemispheric volume were respectively measured using image analysis software (Image J).

Cortex infarct volume %=total cortex infarct volume/total contralateral cortex volume*100

Striatum infarct volume %=total striatum infarct volume/contralateral striatum volume*100

Hemispheric infarct volume %=total hemispheric infarct volume/total contralateral hemispheric volume*100

Correction %=(total contralateral hemispheric volume−(infarction-side total hemispheric volume−infarction-side hemispheric infarct volume))/total contralateral hemispheric volume*100%

GraphPad software Version 6.0 (GraphPad Software, Inc. La Jolla, Calif., USA) was used for statistical analysis of the experimental results. All results are expressed as mean±standard deviation (Mean±SEM). The t-test was used for the statistics between two groups of data, and the one-way ANOVA (Bonferroni post hoc test) was used for the comparison between multiple groups of data. $P<0.05$ indicates significant difference.

As shown by the TTC staining results in FIG. 1, the tissue ischemia and cerebral infarction area of rats receiving SHY01-001 are significantly smaller than those of rats receiving normal saline and metformin hydrochloride.

Figure 2:
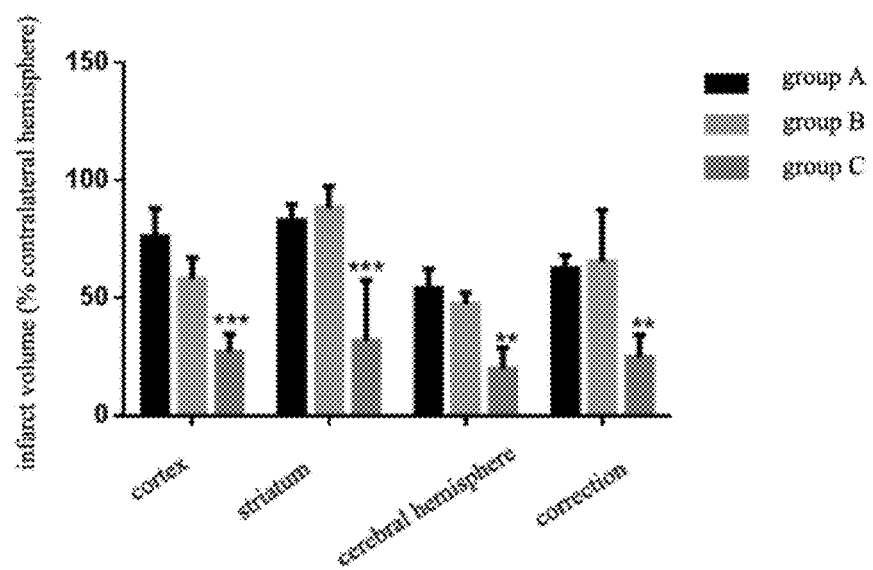
FIG. 2 shows the analysis of cerebral infarction area in rat brain slices.

As can be seen from the further measurements in FIG. 2, the cerebral infarction area of rats receiving SHY01-001 is significantly reduced in the cortex, striatum and cerebral hemisphere compared to rats receiving saline and metformin hydrochloride (FIG. 2:  $P<0.01$, * $P<0.001$). In particular, compared to rats receiving metformin hydrochloride, the cerebral infarction area of rats receiving SHY01-001 decreases by more than 50% in the striatum and cortex. The above results prove that SHY01-001 can effectively reduce the cerebral infarction area.

Example 10

Cytotoxicity Test of Metformin Salt

The methylthiazoletetrazolium (MTT) assay was used to determine the cytotoxicity of various metformin salts.

HEK293T cells were cultured in a 96-well plate, and when the cells were grown to about 60% of the bottom area of the well, 7 compounds in total, including metaformin hydrochloride, SHY01-001, SHY01-002, SHY01-003, SHY01-004, SHY01-005 and SHY01-006 were added at a final concentration of 0.5 mM, 2 mM and 5 mM, and cultured in an incubator at 37° C. and 5% $CO_2$ for 24 hrs. The cell viability was detected by MTT assay to observe the effect of these compounds on the cell activity.

Figure 3:
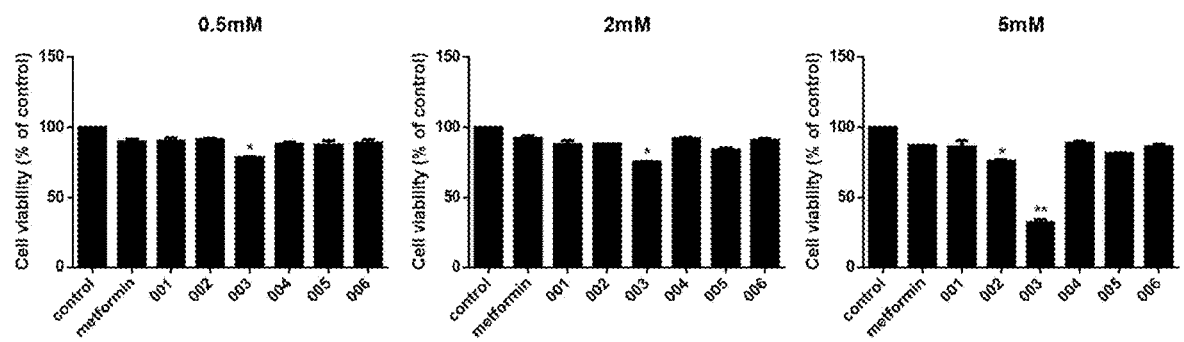
FIG. 3 shows MTT results of SHY01-001.

As shown by the MTT test results in FIG. 3, SHY01-003 (marked as "003" in FIG. 3) at a concentration of 5 mM significantly affects the cell viability, and it also shows an inhibitory effect on the cell viability at both 0.5 mM and 2 mM, indicating that SHY01-003 has high cytotoxicity.

SHY01-001 (marked as "001" in FIG. 3) and other metformin salts do not significantly affect the cell viability, indicating no cytotoxicity at the tested concentrations.

Example 11

Activation Effect of Metformin Salts on p-AMPK Protein

HEK293T cells were cultured in a 6-well plate, and when the cells were grown to about 60% of the bottom area of the well, 7 compounds in total, including metaformin hydrochloride, SHY01-001, SHY01-002, SHY01-003, SHY01-004, SHY01-005 and SHY01-006 were added at a final concentration of 0.5 mM, and 2 mM, and cultured in an incubator at 37° C. and 5% $CO_2$ for 6 hrs. The cells were collected, and lysed, to prepare a protein sample, which was packaged, and stored at −80° C. for test.

Western blot was used to detect the expression level of p-AMPK protein to detect the activation effect of these compounds on p-AMPK protein.

Figure 4:
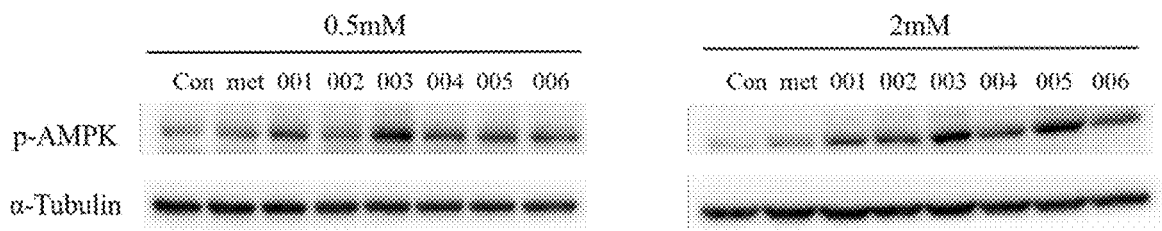
FIG. 4 shows effect of SHY01-001 on the activation of p-AMPK protein.

As shown in FIG. 4, the activation results of p-AMPK protein show that SHY01-001, SHY01-002, SHY01-004 and SHY01-006 (marked as "001," "002," "004" and "006" in FIG. 4) show similar effect in the activation of p-AMPK. Compounds SHY01-003 and SHY01-005 (marked as "003" and "005" in FIG. 4, respectively) have a more pronounced effect on p-AMPK activation.

Example 12

Anti-Inflammatory Effects of SHY01-001 and SHY01-005 on BV2 Microglia Cells The anti-inflammatory effects of Compounds SHY01-001 and SHY01-005 on BV2 microglia cells were compared.

Microglia cell line BV-2 cells were cultured in vitro in a 12-well plate, and then metformin hydrochloride, SHY01-001, SHY01-005, metformin hydrochloride+LPS, SHY01-001+LPS, and SHY01-005+LPS (200 ng/mL) were added to the cell culture medium at a final concentration of 1 mM, and cultured for 24 hrs. The cells were collected to extract proteins, and the protein expression levels of pro-inflammatory factors iNOS and COX-2 were detected.

After LPS stimulation, the state of BV2 microglia cells will change quickly from a resting state to an activated state, and simultaneously express a variety of inflammatory mediators (iNOS, COX-2, and IL-6, etc.) to further activate microglia cells. The activation of microglia cells will aggravate the death of nerve cells associated with ischemia. The reduction in expression levels of iNOS and COX-2 proteins indicates that the inflammatory reaction is inhibited, the microglia activation is reduced, and the cell damage is lowered.

Figure 5:
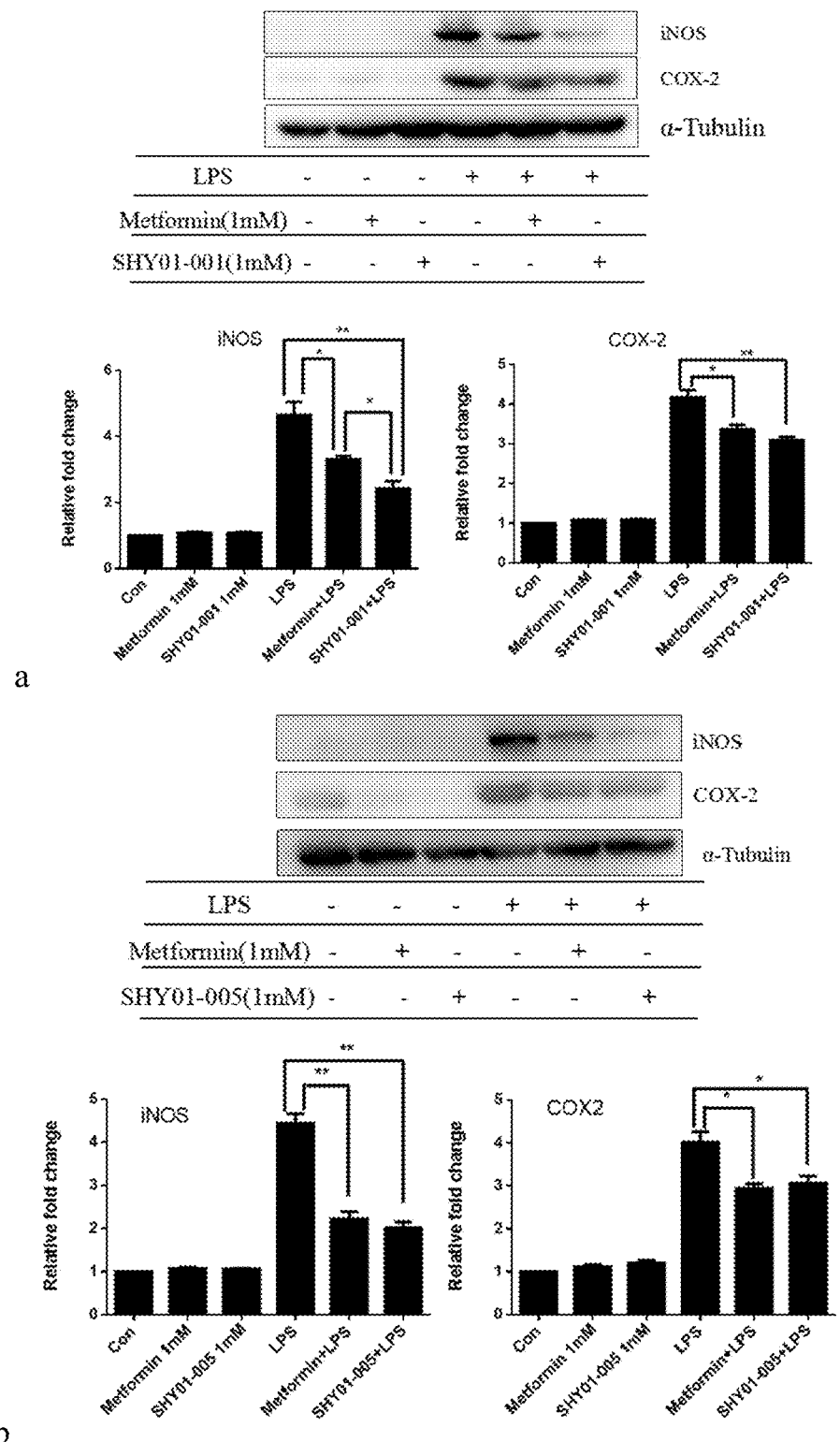
FIG. 5a shows the anti-inflammatory effect of SHY01-001 and metformin hydrochloride on BV-2 microglia cells.
FIG. 5b shows the anti-inflammatory effect of SHY01-005 and metformin hydrochloride on BV-2 microglia cells.

As shown in FIGS. 5a and 5b, SHY01-001 is more potent than metformin hydrochloride in inhibiting iNOS and COX-2 protein expression after LPS stimulation, and the difference is significant. As shown in FIG. 5b, after LPS stimulation, SHY01-005 has the same inhibitory effect on the expression of iNOS protein as metformin hydrochloride, and has a slightly worse inhibitory effect on the expression of COX-2 protein compared with metformin hydrochloride. (**: $p<0.01$, *: $p<0.05$)

Example 13

Test of Solution Stability of SHY01-001 and SHY01-005

An appropriate amount of the samples of metformin hydrochloride or Compound SHY01-001 or SHY01-005 was placed in a 100 ml volumetric flask, and 40 ml of purified water was added, and ultrasonicated to dissolve the content. The solution was warmed to room temperature, diluted to the mark with purified water, shaken until uniform, and allowed to stand in a water bath at 40° C. 10 μl of the test solution was accurately taken at 0, 4, 8, 12, 16, 20, 24, 36, and 48 h, injected it into the liquid chromatograph, and the chromatogram was recorded. The sample content was determined according to the method under the content determination section. The results are shown in Table 4.

As shown in Table 4, the solution of SHY01-001 has excellent stability.

Example 14

Effect of Metformin Monothreonate on Acute Cerebral Ischemia-Reperfusion Injury Narrowing or occlusion of the middle cerebral artery (MCA) is a common cause of stroke in the blood supply area. Reversible middle cerebral artery occlusion (MCAO) was caused by thread embolization method, to establish a focal cerebral ischemia model in rats. SD male rats were used, and blood flow was restored 1.5 hrs after operative ischemia. Within 3 days after operation, The rats were consecutively intraperitoneally injected with 50 mg/kg of the positive control Metaformin, SHY01-001, or magnesium threonate, and the rats in the model control group were given the same dose of saline. The cerebral infarction volume after ischemia-reperfusion in rats was detected by TTC (2,3,5-triphenyltetrazolium chloride) staining.

TTC is a fat-soluble light-sensitive complex, and a proton receptor of the pyridine-nucleoside structural enzyme system in the respiratory chain, which reacts with dehydrogenase in normal tissues and turns red, and has no change and appears pale due to the inability to reaction in ischemic tissues where the activity of dehydrogenase decreases.

24 MCAO rats were divided into four groups, including group A) saline+MCAO group (7 rats); group B) magnesium threonate+MCAO group (6 rats); group C) metformin hydrochloride+MCAO group (7 rats); and group D) SHY01-001+MCAO group (9 rats).

Figure 6:
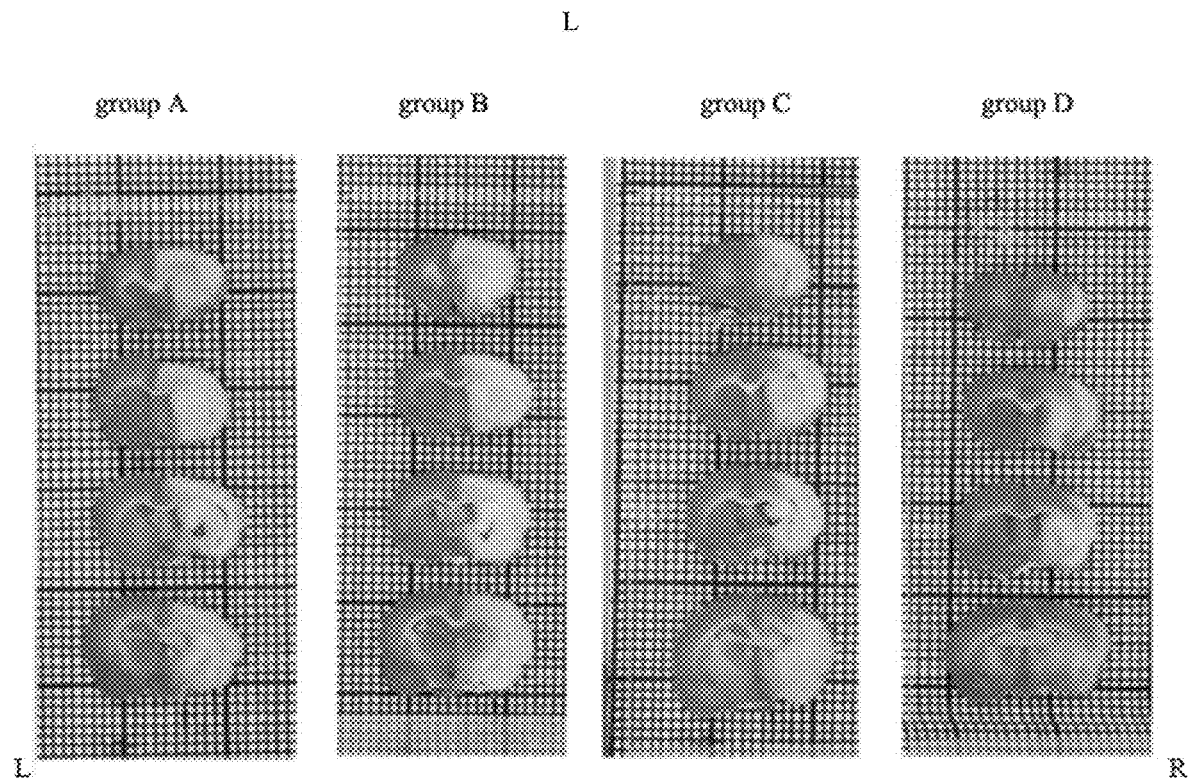
FIG. 6 shows rat brain slices staining with TTC (L and R represent the left and right brain hemispheres respectively).

As shown by the TTC staining results in FIG. 6, the tissue ischemia and cerebral infarction area of rats receiving SHY01-001 are significantly smaller than those of rats receiving saline, metformin hydrochloride, and magnesium threonate.

Figure 7:
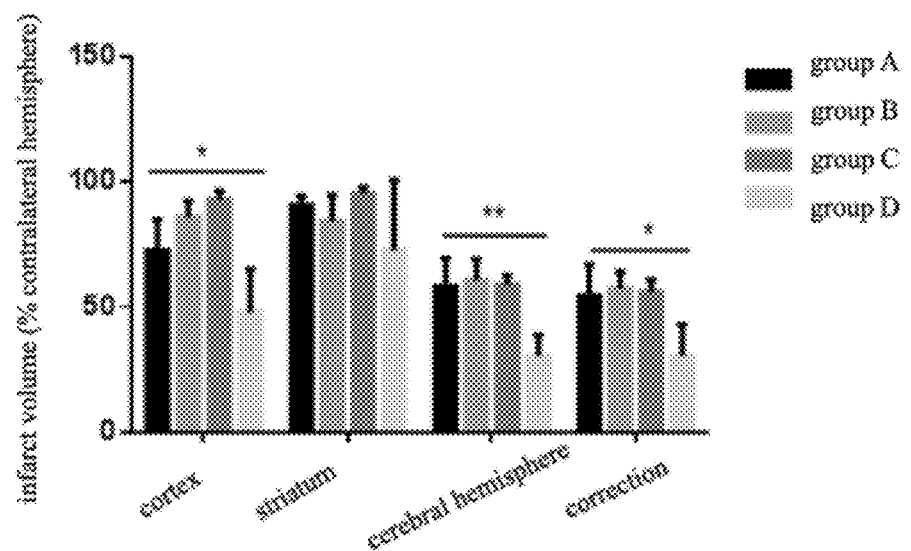
FIG. 7 shows the analysis of cerebral infarction area in rat brain slices.

As can be seen from the further measurements in FIG. 7, the cerebral infarction area of rats receiving SHY01-001 is significantly reduced in the cortex, striatum and cerebral hemisphere compared to rats receiving saline and metformin hydrochloride (FIG. 7: ** $P<0.01$, * $P<0.05$). In particular, compared to rats receiving metformin hydrochloride, the cerebral infarction area of rats receiving SHY01-001 decreases by more than 50% in the cerebral hemisphere. The above results prove that SHY01-001 can effectively reduce the cerebral infarction area.

TABLE 4

Solution stability test results of SHY01-001 and SHY01-005

| Name of Compound | T(h) | 0 | 4 | 8 | 12 | 16 | 20 | 24 | 36 | 48 |
|---|---|---|---|---|---|---|---|---|---|---|
| SHY01-001 | Peak area A | 5190.9 | 5174.7 | 5178 | 5181.8 | 5181.4 | 5180.4 | 5178.8 | 5199 | 5206.9 |
|  | Content % | 100 | 99.7 | 99.8 | 99.8 | 99.8 | 99.8 | 99.8 | 100.2 | 100.3 |
| SHY01-005 | Peak area A | 5189.9 | 5174.7 | 5103.8 | 5081.8 | 5056.3 | 5041.4 | 5023.5 | 5045.4 | 5040.9 |
|  | Content % | 100 | 99.7 | 98.3 | 97.9 | 97.4 | 97.1 | 96.8 | 97.2 | 97.1 |
| Metformin hydrochloride | Peak area A | 5192.9 | 5174.7 | 5123 | 5017.6 | 4989.4 | 4943.6 | 4948.5 | 4945.4 | 4956.8 |
|  | Content % | 100 | 99.6 | 98.7 | 96.6 | 96.1 | 95.2 | 95.3 | 95.2 | 95.5 |

Example 15

Effect of Metformin Monothreonate on Neurological Deficit Caused by Long-Term Ischemia-Reperfusion SD male rats were used, and the rat model of focal cerebral ischemia was established by thread embolization method. Blood flow was restored 1.5 hrs after ischemia. Within 30 days after operation, the rats were consecutively intraperitoneally injected with 50 mg/kg of the positive control Metaformin, SHY01-001, or SHY01-002, and the rats in the model control group were given the same dose of saline. Before modeling, the neurological function of all rats was scored and used as the basic value. On days 1, 7, 14, 21, and 28 after modeling, the neurological behavior test was performed, including: mNSS score, Corner test, and Rota-rod test. On day 30 after modeling, TTC staining was performed to detect the cerebral infarction volume of rats.

Example 16

Metformin Monothreonate Preparations

A. Metformin Monothreonate Tablet
Composition:

| | | |
|---|---|---|
| Metformin monothreonate | 250 mg | |
| Lactose | 40 mg | |
| Dextrin | 30 mg | |
| Corn starch | 90 mg | |
| Povidone K30 | 32 mg | |
| Magnesium stearate | 2 mg | |
| Silica | 3 mg | |

Preparation Process:

Lactose was pulverized, and sieved through a 80 mesh screen for use. The raw materials metformin monothreonate, Dextrin, and Corn starch were respectively sieved through an 80 mesh screen. A prescribed amount of Povidone K30 was weighed and formulated into a 5% solution. Prescribed amounts of metformin monothreonate, Lactose, Dextrin, and Corn starch were weighed and added to a high-efficiency wet granulator, and dry mixed for 6-10 min. The prepared Povidone K30 binder was slowly added, and wet granulation was carried out obtain wet metformin monothreonate granules. The wet granules were dried at a drying temperature of 60-70° C. for 15-30 min. The dried granules were sieved through a 14-mesh screen, to obtain dried metformin monothreonate granules. The dried granules, magnesium stearate, and silica were added to a multi-directional motion mixer, mixed, and tabletted to obtain metformin monothreonate tablets.

B. Metformin Monothreonate Injection
Composition:

| | | |
|---|---|---|
| Metformin monothreonate | 250 mg | |
| Disodium hydrogen phosphate | 180 mg | |
| 0.1M HCl or NaOH | Suitable amount | |

The raw material metaformin monothreonate were pulverized into a fine powder. A sodium dihydrogen phosphate solution was prepared, and the fine powder of metformin monothreonate was dissolved in the sodium dihydrogen phosphate solution. The pH was adjusted to 7-8 with 0.1 M sodium hydroxide or hydrochloric acid, and then transferred to an injection vial, sterilized with steam (at 121° C., for 15 min) to obtain a metformin monothreonate injection.

The present invention has been described in detail in conjunction with the specific embodiments. However, it should be understood that the scope of the present invention is not limited to the foregoing embodiments, and all technical solutions implemented based on the disclosure of the present invention fall within the scope of the present invention.

What is claimed is:

1. A method for preventing and/or treating cerebral infarction in a subject in need thereof, comprising:
administering to the subject a prophylactically and/or therapeutically effective amount of metformin monothreonate of chemical formula (I):

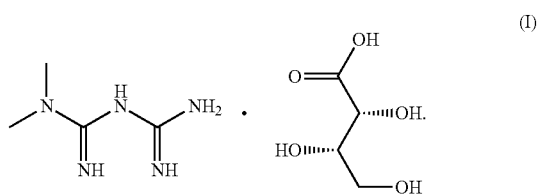

2. The method according to claim 1, wherein the metformin monothreonate is administered in combination with a human tissue-type plasminogen activator.

3. The method according to claim 1, wherein the subject is a non-diabetic patient.

4. The method according to claim 1, wherein the metformin monothreonate is administered orally or by injection.

5. Metformin monothreonate of chemical formula (I):

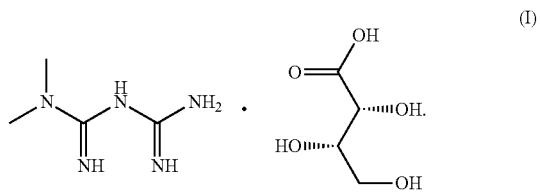

6. A method for preparing metformin monothreonate of chemical formula (I):

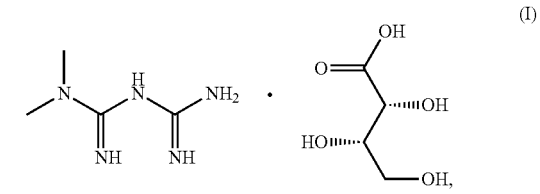

comprising reacting metformin and threonic acid under heating.

7. A pharmaceutical composition, comprising the metformin monothreonate according to claim 5.

* * * * *